United States Patent
Hasenbank et al.

(10) Patent No.: US 7,405,054 B1
(45) Date of Patent: Jul. 29, 2008

(54) SIGNAL AMPLIFICATION METHOD FOR SURFACE PLASMON RESONANCE-BASED CHEMICAL DETECTION

(75) Inventors: Melissa Hasenbank, Free Soil, MI (US); Paul Yager, Seattle, WA (US); Elain Fu, Seattle, WA (US); Kjell Nelson, Seattle, WA (US)

(73) Assignee: University of Washington UW Tech Transfer - Invention Licensing, Seattle, WA (US)

( * ) Notice: Subject to any disclaimer, the term of this patent is extended or adjusted under 35 U.S.C. 154(b) by 204 days.

(21) Appl. No.: 11/301,720

(22) Filed: Dec. 13, 2005

Related U.S. Application Data

(60) Provisional application No. 60/635,595, filed on Dec. 13, 2004.

(51) Int. Cl.
*G01N 33/53* (2006.01)
*G01N 33/553* (2006.01)

(52) U.S. Cl. .......... 435/7.9; 422/82.11; 435/6; 435/7.92; 435/287.2; 435/288.7; 435/808; 436/164; 436/512; 436/514; 436/524; 436/525; 436/805; 436/827

(58) Field of Classification Search .......... None
See application file for complete search history.

(56) References Cited

U.S. PATENT DOCUMENTS

| | | | |
|---|---|---|---|
| 5,304,465 | A | 4/1994 | Garland et al. |
| 5,374,563 | A | 12/1994 | Maule |
| 5,716,852 | A | 2/1998 | Yager et al. |
| 5,972,710 | A | 10/1999 | Weigl et al. |
| 6,454,945 | B1 | 9/2002 | Weigl et al. |
| 6,723,524 | B1 | 4/2004 | Hermens et al. |
| 7,258,837 | B2 * | 8/2007 | Yager et al. .......... 422/57 |

(Continued)

FOREIGN PATENT DOCUMENTS

| WO | WO 98/33941 | 8/1998 |
|---|---|---|

(Continued)

OTHER PUBLICATIONS

Alfonta et al., "Sensing of acetylcholine by a tricomponent-enzyme layered electrode using faradaic impedance spectroscopy, cyclic voltammetry, and microgravimetric quartz crystal microbalance transduction methods," *Anal. Chem.*, 72:927-935 (Mar. 1, 2000).

(Continued)

*Primary Examiner*—Christopher L Chin
(74) *Attorney, Agent, or Firm*—Townsend and Townsend and Crew

(57) ABSTRACT

The present invention provides methods and compositions for amplifying the detection signal in surface plasmon resonance (SPR)-based flow systems. The signal amplification methods comprise the use of well established marker systems that provide a precipitate. The marker systems include, for example, enzyme and nucleation systems. Enzymes suitable for use as a marker system include peroxidases and phosphatases. The amplification system is useful in any SPR-based detection system including microfluidic systems, e.g., "lab on a chip" systems and the like. The methods can comprise any SPR-based assay format, including typical immunoassay formats. The immunoassay formats can include competitive and sandwich assays. Analyte capture agents can include antibodies, lectins, carbohydrates, polynucleotides, receptor proteins, and the like.

39 Claims, 4 Drawing Sheets

U.S. PATENT DOCUMENTS

2004/0053237 A1   3/2004   Liu et al.

FOREIGN PATENT DOCUMENTS

| WO | WO 01/09388 | 2/2001 |
| WO | WO 01/35081 | 5/2001 |
| WO | WO 03/006948 | 1/2003 |
| WO | WO 2004/102193 | 11/2004 |

OTHER PUBLICATIONS

Baggio R., et al., "Induced fit of an epitope peptide to a monoclonal antibody probed with a novel parallel surface Plasmon resonance assay," *J. Biol. Chem.* 280:4188-4194 (2005).

Bardea et al., "Probing antigen-antibody interactions on electrode supports by the biocatalyzed precipitation of an insoluble product," *Electroanalysis* 12:1097-1106 (2000).

Berger, et al., "Surface plasmon resonance multisensing," *Anal. Chem.*, 70:703-706, (1998).

Hutter E., et al., "Role of substrate metal in gold nanoparticle enhanced surface Plasmon resonance imaging," *J. Phys. Chem. B.*, 105:8-12 (2001). E-published Dec. 9, 2000.

Naimushin et al., "Detection of *Staphylococcus aureus* enterotoxin B at femtomolar levels with a miniature integrated two-channel surface plasmon resonance (SPR) sensor," *Biosens. Bioelectron.*, 17:573-584 (Jun. 2002).

Pyo, et al., "Multichannel surface plasmon resonance imaging and analysis of micropatterned self-assembled monolayers and protein affinity interactions," *Langmuir*, 21:166-71 (Jan. 4, 2005). E-published Dec. 8, 2004.

Rella R., et al., "Liquid phase SPR imaging experiments for biosensors applications," *Biosens. Bioelectron.*, 20(6):1140-1148 (Dec. 15, 2004).

Rooney J. and Hall E., "Surface plasmon resonance: theoretical evolutionary design optimization for a model analyte sensitive absorbing-layer system," *Anal. Chem.*, 76(23):6861-6870 (Dec. 1, 2004).

Smith A., et al., "Surface Plasmon resonance imaging studies of protein-carbohydrate interactions," *J. Am. Chem. Soc.*, 125:6140-6148 (2003).

Kim et al., "Enhanced sensitivity of surface plasmon resonance (SPR) immunoassays using a peroxidase-catalyzed precipitation reaction and its application to a protein microarray," *J. Immunol. Meth.* 297:125-132 (2005).

Loo et al., "An enzyme-amplified diffraction-based immunoassay," *Anal. Biochem.* 337:338-342 (2005).

Patolsky et al., "Precipitation of an insoluble product on enzyme monolayer electrodes for biosensor applications: characterization by faradaic impedance spectroscopy, cyclic voltammetry, and microgravimetric quartz crystal microbalance analyses," *Anal. Chem.* 71:3171-3180 (1999).

Su and O'Shea, "Determination of monoenzyme- and bienzyme-stimulated precipitation by a cuvette-based surface plasmon resonance instrument," *Anal. Biochem.* 299:241-246 (2001).

\* cited by examiner

A  B  C

A B

SIGNAL AMPLIFICATION METHOD FOR SURFACE PLASMON RESONANCE-BASED CHEMICAL DETECTION

CROSS REFERENCES TO RELATED APPLICATIONS

The present application claims priority to U.S. Provisional Patent Application No. 60/635,595, filed Dec. 13, 2004, the entire disclosure of which is incorporated by reference herein.

STATEMENT AS TO RIGHTS TO INVENTIONS MADE UNDER FEDERALLY SPONSORED RESEARCH AND DEVELOPMENT

Aspects of the present invention were conducted with funding provided by the National Institutes of Health, National Institute of Dental and Craniofacial Research under Grant Nos. 5U01 DE0-14971-03 and DE07023-28. The Government may have certain to rights in the claimed invention.

BACKGROUND OF THE INVENTION

The present invention relates generally to microfluidic devices and flow-based methods for performing analytical testing and analysis and, more specifically, the present invention provides compositions and methods for signal enhancement of surface plasmon resonance-based chemical detection in flow-based systems, such as microfluidic flow devices.

Surface plasmon resonance (SPR) is a general spectroscopic method for sensing refractive index changes near the surface of a metal film. Its sensitivity to these changes provides a versatile platform for the observation and quantitation of chemical reactions and intermolecular binding at the metal/solution interface. The generality of the technique has led to its application to a variety of chemical systems, including biological interactions and reactions. Several specifically designed commercial instruments are currently available for these types of assays.

SPR allows detection of small changes in refractive index that result from interactions between surface-bound biomolecules and a solution-borne binding partner. For example, immobilization of a protein to the sensor surface allows for detection of protein binding events manifested by a change in refractive index that is measured as a change in the angle-dependent (or wavelength-dependent) reflectance of the metal film. This type of SPR sensing is typically carried out on commercial instruments that can use, for example, a binding or immobilization layer, such as a carboxylated dextran gel, in addition to a gold film as the sensor surface. Where the dextran gel is used, the gel acts as a host for the surface-immobilized binding partner. However, SPR has also been applied in a number of other formats, including imaging SPR where a large number of chemistries can be rapidly interrogated simultaneously. Also, a variety of other surface chemistries have been used to immobilize and pattern biomolecules for interaction with their binding partners.

SPR relies on the optical excitation of surface modes (plasmons) in a free electron metal, e.g., gold (Au), silver (Ag), aluminum (Al), or copper (Cu) anchored to a glass substrate. Methods for attaching or anchoring the metal to the glass substrate are well known in the art and can include adhesion with a thin layer of, for example, mercaptosilane, titanium, or chromium. Back-side, p-polarized illumination of a prism-coupled film at a specific angle greater than the critical angle for total internal reflection results in plasmon excitation at the metal-solution interface. SPR is most easily observed as a reduction in the intensity of reflected light as measured at the detector (located in the path of the reflected light). The experimental condition (angle or wavelength) of minimum reflectivity, denoted as the SPR angle, shifts to a different position as material is adsorbed onto the metal layer. The shift in the resonance position can be converted to a measure of the thickness of the adsorbed material using various calculations, e.g., complex Fresnel calculations. Adsorption, desorption, and molecule-molecule interactions that occur within the sensing region of about 300 nm adjacent to the metal-solution interface, can thus be monitored in real-time, making SPR suitable for dynamic sensing.

In using SPR to test for biological, biochemical, or chemical substances, a beam of light from a laser source is directed through a prism onto a biosensor consisting of a transparent substrate, usually glass, which has one external surface covered with a thin film of a noble metal, which in turn, is covered with an organic film that interacts strongly with an analyte, such as a biological, biochemical, or chemical substance. The organic film can contain substances, such as antibodies or antigens, that can bind with an analyte in a sample solution to cause an increase in the refractive index in the sample sensing region and shift the SPR resonance. By monitoring either the position of the SPR resonance (as a function of the experimental parameter angle or the wavelength) or the reflectivity at fixed experimental parameters near the SPR resonance, the presence or absence of an analyte in the sample can be detected. Typically, labeling of biomolecules is not required, nor has it been desired. However, this limits the changes in refractive index produced by the binding of both analytes and secondary reagents, which, in turn, limits the speed and sensitivity of SPR detection.

Materials and products have been proposed to enhance the signal from standard SPR-detection methods. One such method is described in WO 01/09388 (incorporated herein by reference), wherein metal nanoparticles are used as optical tags.

The present invention provides additional compositions and methods for signal enhancement of surface plasmon resonance-based chemical detection systems. In the methods an enzyme precipitation signal-enhancement protocol that is well established for use in optical absorption assays is shown to increase the signal associated with reflectivity changes in chemical assays, especially biomolecular recognition assays on planar SPR surfaces coated with a capture reagent. The methods are generally applicable to all detection schemes in which an enzyme label can be used. Commonly used detection schemes in which this method is applicable include, but are not limited to: i) a competition or displacement assay with an enzyme labeled ligand, ii) a sandwich assay in which the enzyme is linked to an agent that binds specifically to the analyte of interest, i.e., an antibody, and iii) a nucleic acid assay in which the enzyme is linked to a nucleic acid probe fragment.

BRIEF SUMMARY OF THE INVENTION

The present invention provides signal amplification methods and compositions for surface plasmon resonance (SPR)-based chemical detection in flow-based systems, such as microfluidic systems. The signal amplification is provided using well established precipitation methods. In certain embodiments of the present invention the methods for conducting an assay for an analyte in a test solution that may contain the analyte comprise: i) providing a surface plasmon resonance (SPR) active surface; ii) immobilizing an analyte capture agent on the surface; iii) contacting the analyte capture agent with the test solution and a reagent labeled with an enzyme under conditions for the analyte capture agent to form a complex, wherein the enzyme is capable of forming a precipitate when reacted with a precipitatable substrate; iv) contacting the complex with a solution comprising the precipitatable substrate of the enzyme under conditions conducive to the formation of the precipitate product for a time period sufficient for forming the precipitate; and v) detecting a change in refractive index near the surface using a SPR signal.

The surface plasmon resonance surface can be a thin metal film. In typical embodiments of the invention the thin metal film is gold, silver, aluminum or copper. A glass surface, such as glass slide is typically used.

The enzyme labeled reagent can be the analyte of interest or an analyte binding agent. In certain embodiments of the invention the analyte binding agent is an antibody, a lectin, a carbohydrate, a polynucleotide sequence, or a receptor protein. Antibodies typically useful in the methods include a polyclonal antibody, a monoclonal antibody, an antibody antigen-binding fragment, or a recombinant antibody. The antibody antigen-binding fragment can be a Fab, F(ab')2, a Fab', or a Fv fragment, and the like.

In typical embodiments of the invention, the analyte capture agent is an antibody, a lectin, a carbohydrate, a polynucleotide sequence, or a receptor protein. As with the enzyme labeled reagent, the antibody can be a polyclonal antibody, a monoclonal antibody, an antibody antigen binding fragment, or a recombinant antibody and the useful antibody antigen binding fragments include a Fab, F(ab')2, a Fab', or a Fv fragment, and the like.

The methods of the invention typically use as the enzyme a peroxidase or a phosphatase. Although other enzymes with precipitatable substrates can also be used. Enzymes particularly useful in the methods of the invention are horseradish peroxidase or alkaline phosphatase. Tetramethyl-benzidine is a typical enzyme substrate that can be used with a peroxidase and 5-bromo-4 chloro-3-indolylphosphate with nitroblue tetrazolium can be used as the substrate for a phosphatase, such as alkaline phosphatase.

In one typical embodiment of the present invention the analyte capture agent is a monoclonal antibody and the enzyme labeled reagent is the analyte of interest. In this embodiment of the invention, the enzyme labeled analyte can be added to the analyte capture agent prior to the test solution for a time period sufficient for complex formation. When the test solution is added, analyte present in the solution competes with the enzyme labeled analyte for binding to the antigen capture agent. The amount of analyte in the test solution is detected by a reduction in the SPR signal as compared to a control reaction.

In another embodiment of the present invention, the test reaction is a sandwich assay. In this embodiment, the analyte capture agent and the enzyme labeled analyte binding agent are specific for the analyte of interest. In one example, the analyte capture agent and the enzyme labeled analyte binding agent are both monoclonal antibodies specific for the analyte of interest. In still another embodiment of the invention, the analyte capture agent is a polynucleotide sequence and the enzyme labeled reagent is a nucleic acid probe.

Another embodiment of the present invention provides a method for associating a plurality of analytes on spatially discrete regions of a surface. The method comprises: i) providing a surface plasmon resonance active surface; ii) immobilizing a plurality of analyte capture agents on the surface in discrete regions to form an array; iii) contacting the analyte capture agents with a test solution and a plurality of enzyme labeled reagents specific for the analytes of interest, under conditions for analyte capture agents to form specific complexes, wherein the plurality of enzyme labeled reagents are capable of forming a precipitate when reacted with a precipitatable substrate; iv) contacting the complexes with the precipitatable substrate under conditions conducive to formation of the precipitate product for a time period sufficient for precipitate formation; and v) detecting a change in refractive index near the surface at each discrete region using a SPR signal. As with the prior methods the surface plasmon resonance surface can be a thin metal film, such as, gold, silver, aluminum or copper, and the like. Typically, the thin metal film is coated on a glass surface.

In one embodiment of this aspect of the invention, the enzyme labeled reagents are an analyte of interest or an analyte binding agent. The analyte binding agents can be antibodies, lectins, carbohydrates, polynucleotide sequences, or receptor proteins. Antibodies useful in these embodiment of the invention comprise polyclonal antibodies, monoclonal antibodies, antibody antigen-binding fragments, or recombinant antibodies, and the like. The antibody antigen-binding fragments can be Fab, F(ab')2, Fab' or Fv fragments, among others.

The methods for screening a plurality of analytes can also comprise the use of an antibody, a lectin, a carbohydrate, a polynucleotide sequence, or a receptor protein as the analyte capture agent. Polyclonal antibody, monoclonal antibody, antibody antigen-binding fragment, and recombinant antibody are also useful in this regard. The antibody antigen-binding fragment can be Fab, F(ab')2, a Fab', or a Fv fragments, and the like.

In this aspect of the invention the enzyme can be a peroxidase or a phosphatase. Although other enzymes that have precipitatable substrates are also useful. Horseradish peroxidase or alkaline phosphatase are particularly useful. Precipitatable substrates include tetramethyl-benzidine for peroxidase enzymes and 5-bromo-4 chloro-3-indolylphosphate with nitroblue tetrazolium for the phosphatases.

In certain embodiments of the invention for screening a plurality of analytes, the analyte capture agents comprise monoclonal antibodies and the enzyme labeled reagents are the analytes of interest. In one embodiment, the enzyme labeled analyte is added prior to the test solution for a time period sufficient for complex formation. Once the analyte in the test solution contacts the complexes on the surface, the analyte competes with the enzyme labeled analyte for binding to the antigen capture agent.

In another embodiment, the analyte capture agent and the enzyme labeled analyte binding agent are specific for the analyte of interest. In one example, the analyte capture agent and the enzyme labeled analyte binding agent are both monoclonal antibodies specific for the analyte of interest. The analyte capture agent can also be a polynucleotide sequence and the enzyme labeled reagent is a nucleic acid probe.

In still another embodiment of the invention a method for high throughput screening of compound libraries to identify compounds of interest having a positive response for a pre-selected activity is provided. The method comprises: i) providing a surface plasmon resonance (SPR) active surface; ii) contacting a plurality of screening assays on the surface whereby a plurality of members of the compound library are associated with the surface, the screening assays established to form an enzyme precipitate when reacted with a compound from the library; iii) detecting change in refractive index near the surface at each discrete region using a SPR signal; and iv) selecting compounds having a positive response for the pre-selected activity.

BRIEF DESCRIPTION OF THE DRAWINGS

FIG. 3A shows the three microchannels filled with PBS prior to exposure to substrate. FIG. 3B shows the three microchannels following addition of substrate and rinsing.

Figure 1:
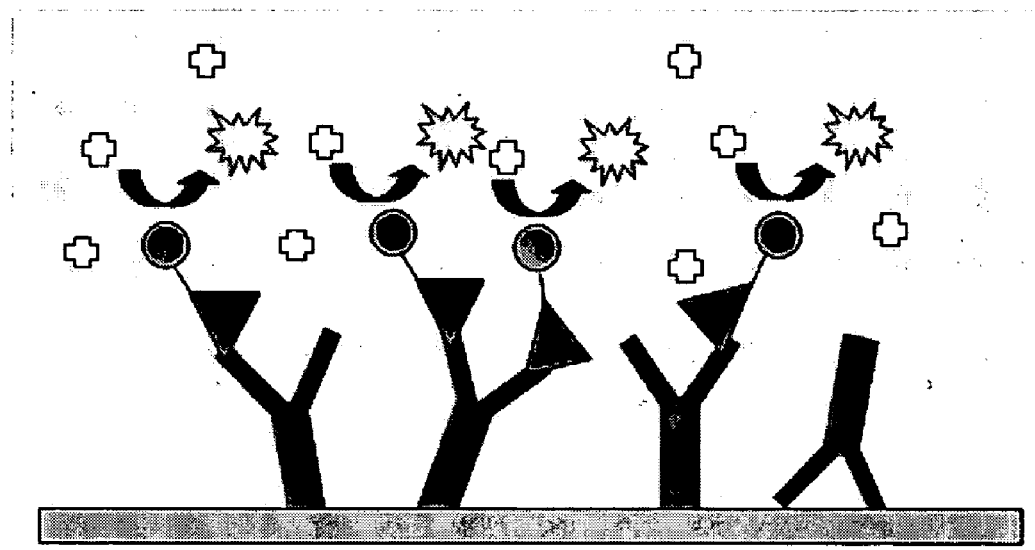
FIG. 1 depicts the surface immobilization scheme used to demonstrate the utility of the signal amplification method. A legend is included in FIG. 1 identifying analyte capture agent (e.g., "anti-cortisol"), enzyme labeled reagent (e.g., "cortisol-HRP"), precipitable substrate (e.g., "TMB"), and precipitate product (e.g., "EIA Product"), according to an exemplary embodiment of the invention.
Figure 1:
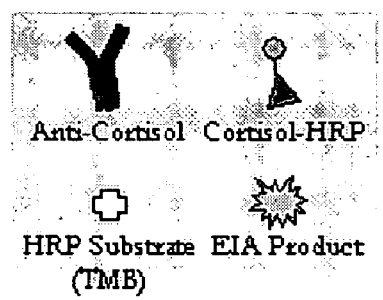

A further understanding of the nature and advantages of the invention will become apparent by reference to the remaining portions of the specification.

DETAILED DESCRIPTION OF THE INVENTION

The present invention provides a signal amplification method and compositions for surface plasmon resonance (SPR)-based chemical detection in a flow-based system, e.g., microfluidic device. The signal amplification is provided using well-established precipitation methods, including enzyme precipitation assays (Alfonta et al., *Anal. Chem.* 72:927-935, 2000; Bardea et al., *Electroanalysis* 12:1097-1106, 2000). Results provided herein demonstrate that these methods can result in a significant enhancement of the SPR signal, and that the signal amplification techniques described herein are suitable for use in a flow-based system.

The methods of the present invention are generally applicable to all analyte detection schemes in which a precipitatable marker can be used; for example, where a precipitatable enzyme product can be used. Three commonly used detection schemes in which this method are applicable: i) a competition or displacement assay with an enzyme labeled ligand, ii) a sandwich assay in which the enzyme is linked to a binding partner specific for an analyte of interest, and iii) a nucleic acid assay in which the enzyme is linked to a nucleic acid probe.

The components of the signal amplification system of the present invention comprise i) an enzyme or molecule that provides a center for nucleation linked to a component of the specific detection scheme, ii) an enzyme substrate or monomer subunit of the nucleation reaction, iii) the product of the enzyme reaction or nucleation reaction on the substrate, an insoluble precipitate, and iv) the SPR-based detector. For all detector schemes, addition of the substrate to the sensing cell will allow the surface immobilized enzyme to act on the substrate or the nucleation reaction to proceed to produce an insoluble precipitate product. The product can diffuse and adsorb to the sensing SPR-based detector surface and create a significant increase in the effective refractive index within the SPR sensing volume (sensing depth is about 300 nm into the sample from the metal surface), thus amplifying the original SPR signal.

A typical substrate for a surface plasmon resonance imaging sensor useful in the present invention comprises any material in which the phenomenon of surface plasmon resonance can be observed, i.e., the optical excitation of surface modes (plasmons) in a free electron metal when coupled to a prism. In typical embodiments of the present invention, SPR substrates comprise free electron metal films deposited or seeded onto a glass surface. Free electron metals include, but are not limited to, gold, silver, aluminum and copper. The present invention also encompasses the use of alloys or mixtures of metals. The substrate will also include a molecular coupling system specific to the detection scheme being used.

The term "prism" as used herein is meant to comprise any element optically coupled with the SPR substrate through which incident light is directed in order to establish the conditions necessary to excite a surface plasmon, e.g., a polished SF11 glass slide onto which a film of gold has been evaporated or seeded. It should be noted that SPR substrates are commercially available and are compatible with the methods of the present invention.

An important aspect of the present invention is the ability to use the methods of the present invention in multiplex assays. Spatial multiplexing, i.e., arrays, is made possible by the physical separation of reagents on the metal substrate. However, additional multiplexing can be achieved by using the signal enhancement methods of the present invention. The methods of the present invention can also be used in microfluidic devices that comprise a SPR imaging assembly. Many microfluidic, or "lab on a chip" devices are well known in the art. See for example, U.S. Pat. Nos. 5,972,710 and 5,716,852, 6,454,945, and WO03/006984, the entire disclosures of each of which are incorporated by reference herein.

The present invention encompasses a variety of different assay methods. In particular, the methods comprise various formats of immunoassay methods. These methods typically provide for the binding of an analyte to the SPR imaging surface either directly or through an intermediary binding partner. The binding partner can include, for example, an antibody, a lectin, a receptor protein, a nucleic acid sequence, a carbohydrate, glycoprotein, and the like. The binding partner, if used, can be attached to the SPR imaging surface in advance. Alternatively, the binding partner is bound to the SPR imaging surface subsequent to having been reacted with the analyte, if present.

Further, a second binding partner specific for the analyte can be used. The second binding partner can be an antibody, antigen-binding fragment or recombinant antigen-binding molecule derived from an antibody. For example, the antibody can be polyclonal or monoclonal. Or, a binding fragment thereof can include a Fab, F(ab')$_2$, Fab', Fv, or single chain antigen-binding fragment thereof, the antibody can also be a chimeric antibody, or antigen-binding fragment thereof, or can be a humanized antibody, or antigen-binding fragment thereof. A derived recombinant antigen-binding molecule can include single chain antibodies, or any recombinantly-produced antigen-binding molecule that comprises the antigen binding region of an antibody that specifically recognizes or binds to the analyte of interest.

The second binding partner of the analyte can carry the marker or enzyme. Alternatively, the enzyme can be carried by an agent capable of binding to the second binding partner of the analyte. For example, if the second binding partner of the analyte is a murine monoclonal antibody against the analyte, the enzyme can be attached directly to the monoclonal antibody, or alternatively can be attached to an anti-mouse IgG antibody, and the like.

In one embodiment of the invention, the enzyme comprises a horseradish peroxidase with 3,3',5,5'-tetramethyl-benzidine (TMB) as the substrate. Other substrates may be used in combination with horseradish peroxidase and include, for example, 4-chloro-1-naphthol (4-CN) and 3,3'-diaminobenzidine (DAB). However, the subject invention encompasses other enzyme-substrate system combinations that produce a precipitate on the solid surface. For example, formation of a precipitate can be the result of nucleation, by nucleated growth of metal, or non-metal particles, or the result of chain or polymerization reactions. Different enzyme-substrate combinations can include for example, but are not limited to, alkaline phosphatase as the enzyme and 5-bromo-4 chloro-3-indolylphosphate with nitroblue tetrazolium as the substrates. Other peroxidase enzymes can also be used. In addition, non-enzyme systems that would produce a precipitate can also be used, such as for example, nucleation reactions.

FIG. 1 schematically illustrates an embodiment of the signal enhancement method of the present invention. According to the embodiment, analyte capture agent is immobilized on an SPR active surface, for example, within a channel of a microfluidic device. In operation of the device, test solution and enzyme labeled reagent are contacted with the immobilized analyte capture agent under conditions suitable for the analyte capture agent to form a complex including analyte capture agent and enzyme labeled reagent or analyte. After formation of complex, solution including a precipitatable substrate of the enzyme is contacted with the complex under conditions conductive to the formation of a precipitate product for a time period sufficient to form a precipitate. Even under flow conditions, precipitate accumulated on the SPR active surface may be detected, for example, by detecting a change in refractive index near the surface using a SPR signal.

According to the particular embodiment illustrated in FIG. 1 and set forth in the embodiment described in Examples 1 and 2 (see below), the enzyme exemplified was horseradish peroxidase (HRP) and the substrate 3,3',5,5'-tetramethyl-benzidine (TMB). An enzyme-cortisol complex, used as an analyte capture agent, was immobilized to the sensing surface of a microfluidic device.

A microfluidic device typically includes a microfluidic channel having a plurality of inlets for receiving different fluid flows. Under microfluidic conditions, fluids typically flow in a very predictable, laminar fashion, thereby allowing one or more fluids to flow in a channel without turbulent mixing. Movement of particles in a fluid within a microfluidic channel is predictable and occurs mainly by diffusion, for example, in directions perpendicular to the direction of flow.

Different ways of manufacturing microfluidic devices are available, including, for example, traditional lithographic techniques, soft lithography, laminate technologies, etc. A microfluidic channel can be formed, for example, in a Mylar® ACA sheet that has a thickness between about 50 μm to about 100 μm. The Mylar® ACA sheet may be cut to create the microfluidic channel which is then fixed directly to a gold-coating on a glass substrate, such as a microscope slide. The gold coating provides the sensing surface for the SPR imaging (SPRI) assembly. The gold coating can have a range of thicknesses, but is typically about 45 nm thick for detecting biomolecular interactions in aqueous solutions. The sensing surface is then coated with an analyte capture agent (e.g. anti-cortisol antibody) and the enzyme labeled reagent (e.g., enzyme-cortisol complex) is adsorbed to the sensor surface by the analyte capture agent. A substrate, such as TMB (see, e.g., Examples 1 and 2) is added to the sensing cell or microfluidic channel and the reaction monitored. Finally, the substrate can be rinsed from the sensing cell and the signal amplification due to the precipitate formation and adsorption to the sensing surface can be quantitated using, e.g., SPR imaging.

The following examples are intended to illustrate but not limit the invention.

EXAMPLE 1

In this non-limiting example an anti-cortisol monoclonal antibody is utilized as an analyte capture agent and immobilized on a gold coated glass SPR sensor surface and a horseradish peroxidase labeled cortisol is incubated with the immobilized antibody. Subsequently the enzyme substrate tetramethyl-benzidine (TMB) is added and the reaction is allowed to proceed to form an insoluble blue product. The assay demonstrates that the precipitate formed by the enzymatic reaction adsorbs to the SPR sensor surface amplifying the detection signal.

Briefly, the gold coating of a microscope slide is cleaned in a base/peroxide wash. In such a method, in a clean, flat-bottom glass dish, hydrogen peroxide, ammonium hydroxide, and double distilled water (ddH$_2$O) were mixed in a 1:1:5 volumetric ratio. The solution was heated to about 65° C. and covered with a watch glass to minimize evaporative loss. The gold-coated glass slide was immersed in the heated solution and soaked for approximately 10 minutes. The slide was removed and washed with ddH$_2$O followed by absolute ethanol. Finally, the slide was blow dried under a dry stream of N$_2$.

The flow cell was composed of three layers. A first Mylar® ACA layer into which the channels were defined was attached to a Mylar®-only layer containing the inlet/outlet ports. This assembly was then attached to a gold-coated glass slide. The edges of the Mylar® ACA layer may thereafter be pressed to the edges of the gold coating to ensure a good seal around the edges of the microfluidic channel.

The microfluidic channel may then be treated upstream of a sensing surface so as to reduce, and preferably prevent the adsorption of the solution phase cortisol-horseradish peroxidase complex to the surface upstream of the sensing surface. Many known methods of preventing the adsorption of proteins or analytes to a gold coating may be used. For example, the gold coating upstream of the sensing surface may be coated with ethylene-oxide terminated self-assembling molecule ("SAM") prior to assembly, if desired.

The sensing surface of the flow cell assembly was then coated with the monoclonal antibody specific for cortisol (0.5 mg/ml). The monoclonal antibody was introduced into the microfluidic channel using a syringe. The flow cell assembly was allowed to sit undisturbed, face up, covered, for 30 minutes. Thereafter, the remaining coating solution was rinsed out of the microfluidic channel with an excess of buffer. The flow cell was then incubated with a blocking step comprising 5 mg/ml BSA for 30 min and the flow cell was again rinsed.

The flow cell was then loaded with 5.6 μg/ml cortisol-HRP in phosphate buffered saline (PBS) and incubated for 30 min prior to rinsing away the excess cortisol-HRP complex. Subsequently, 1.13 mM tetramethyl-benzidine substrate in acetate buffer was added and incubated for various time periods.

Separate control experiments were also run where a cortisol-BSA complex was incubated with the anti-cortisol antibody.

Figure 2:
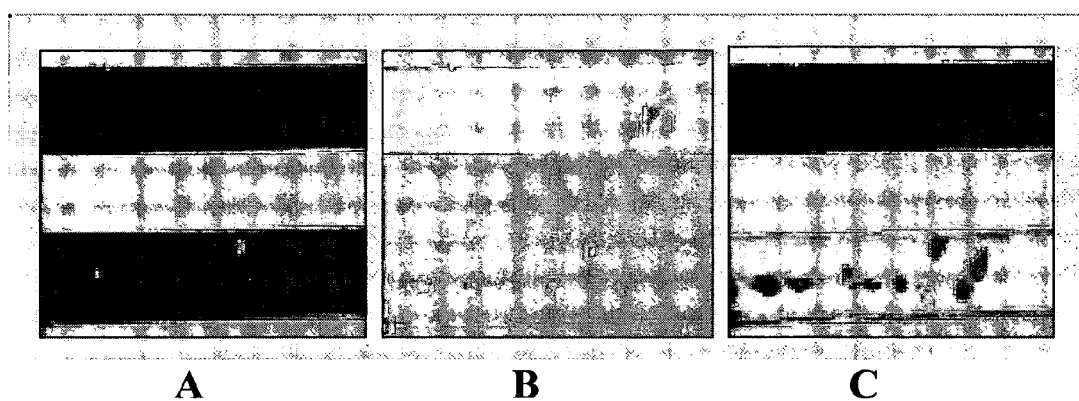
FIG. 2 provides surface plasmon resonance images showing a significant increase in signal due to precipitate adsorption to the surface (difference between right and left images). A series of SPR images are shown. In each image, the top channel is a control channel into which cortisol-BSA was added in place of cortisol-HRP complex. The two channels were otherwise exposed to the same treatments.

The significant signal enhancement due to this method is illustrated in FIG. 2. In each panel in FIG. 2 (FIGS. 2A, 2B, and 2C), two microfluidic channels are identified as two darker regions separated by a brighter region. The brighter region separating the two channels represents adhesive and Mylar™ layers comprising the microchannel walls. The top channel in each of FIGS. 2A, B, and C is a control channel having immobilized cortisol-BSA and the bottom channel in each of the figures contains immobilized cortisol-HRP. The left most image (FIG. 2A) showed the channels filled with PBS. The center image (FIG. 2B) shows the two channels filled with TMB solution. It is noted that the TMB solution itself has a high refractive index so produced a change in the effective refractive index sensed by SPR when in the channel. Therefore, the two channels appear "brighter" in FIG. 2B than in FIG. 2A. The image on the right (FIG. 2C) shows the channels filled with PBS after exposure to the TMB substrate and extensive rinsing with PBS. As is obvious from the images, the top, control channel that only contained immobilized cortisol-BSA and substrate (i.e., no enzyme) showed little change in signal, while the bottom channel that contained surface immobilized enzyme and substrate, and which appears "brighter" in FIG. 2C, showed a large change in signal. Quantitation of the change in reflectivity due to the precipitate indicated the precipitate produced a greater than 50% change in reflectivity. As a comparison, a monolayer of antibody non-specifically adsorbed directly onto the metal sensing surface produced a change in reflectivity of about 35%. Thus, the results indicate that the current method allows significant amplification of signal well beyond what would be expected from analyte binding followed by standard antibody labeling techniques.

This particular embodiment was demonstrated using stopped flow conditions in a uniformly patterned microfluidic channel with SPR imaging. However, the scope of its utility is significantly broader. This method can be used with any SPR-based detection method, both imaging and non-imaging. Further, in the case of SPR-imaging, the methods of the present invention are compatible with surface patterning such that the analyte of interest is only located in discrete regions of the sensing surface, as discussed above. Preliminary results indicate that the precipitate once formed adsorbs to the sensing surface and is then surprisingly resistant to subsequent rinsing. As such, the methods should be compatible with detection under conditions of flow and, therefore, are useful in flow-based systems, such as microfluidic systems and devices.

The present methods hold several distinct advantages over existing methods of signal amplification for SPR-based detection. First, the use of a low molecular-weight substrate such as TMB results in quick diffusion to the surface-immobilized enzyme; this is a fast amplification step as compared to the established method of amplification using secondary antibodies (which are about 500 times more massive, and therefore diffuse more slowly to the surface). The preliminary results indicate that the reaction and precipitate formation for this specific set of conditions occurs within about 15 seconds after the application of the TMB to the surface, as compared to greater than 30 minutes for amplification with secondary antibodies (Naimushin et al., *Biosens. Bioelectron.* 17:573-584, 2002). Second, the precipitate product is not restricted to the site of its formation, like secondary antibody tags, and can thus diffuse closer to the surface and adsorb as compared to tethered particle tags. Since the sensitivity of SPR decays exponentially with distance from the metal sensing surface, the proximity of the precipitate to the metal surface is critical. Moreover, the precipitate immobilized to the surface is resistant to rinsing. Therefore, the current methods are suitable for use in flow-based systems.

EXAMPLE 2

The present example further illustrates the utility of the enzyme precipitation and signal amplification methods of the invention for quantification of low concentrations of analytes under microfluidic laminar flow conditions. In general, these results further demonstrates the utility of the current methods, illustrating that the rapid and significant amplification of the SPR signal remains robust in flow-based assays.

The overall experimental method, including reagents and detection technique, is substantially similar to that described in Example 1 (see above). A multi-channel microfluidic flow cell constructed from laminate sheets of Mylar™ and adhesive and a gold-coated glass slide was used in these experiments. In a first step, anti-cortisol antibodies, utilized as exemplary analyte capture agent, were physically adsorbed to the gold sensor surface by incubating a 0.1 mg/ml solution in the microchannels for 30 minutes. After rinsing thoroughly with phosphate buffered saline (PBS) to remove any excess and/or loosely bound antibodies, a 5 mg/ml BSA solution was introduced into each of the microchannels for another 30 minutes to block any remaining binding sites on the gold surface. After rinsing with PBS, a range of concentrations of cortisol-horseradish peroxidase (c-HRP) conjugate in PBS (including 0.5 µg/ml and 0.07 µg/ml), were then introduced into the microchannels and allowed to incubate for 30 minutes. During this process, the cortisol-HRP conjugate was expected to bind specifically to the surface-immobilized anti-cortisol antibody molecules. As a control experiment, a BSA solution was introduced in place of the c-HRP conjugate in one of the microchannels. After rinsing thoroughly to remove any excess c-HRP molecules, 0.2 ml of a solution containing 1.13 mM TMB plus hydrogen peroxide in excess and additional proprietary agents (United States Biological, Swampscott, Mass., USA) was pumped through each microfluidic flow cell at a controlled rate of 1 µl/s (using syringe pumps). As in the Example 1 (see above), the sensor surface was monitored via the SPR microscope throughout the course of the enzyme precipitation reaction and formation of the insoluble blue product. The TMB solution was subsequently rinsed from each of the microfluidic channels with an excess of PBS at a volumetric flow rate of about 1 µl/s. The signal amplification due to the precipitate formation and adsorption to the gold sensor surface was examined both qualitatively and quantitatively using SPR imaging (see, e.g., FIGS. 3 and 4).

Figure 3:
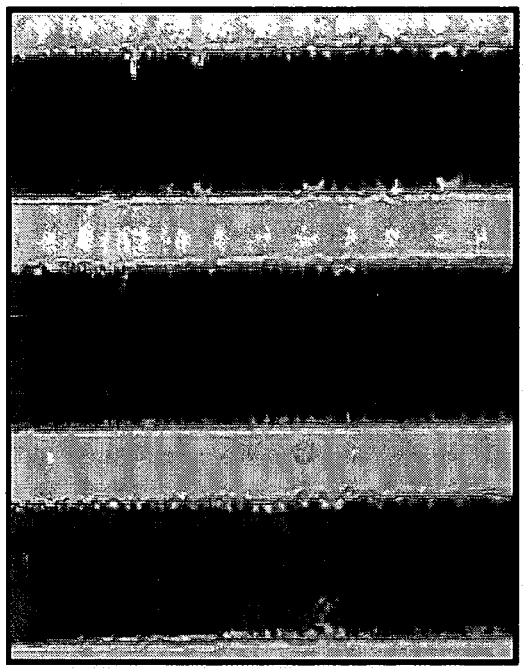
FIG. 3 provides SPR images showing an increase in signal due to precipitate adsorption on the microchannel surface under conditions of flow. Three microchannels (top, middle, bottom) were exposed to various concentrations of enzyme labeled reagent.
Figure 3:
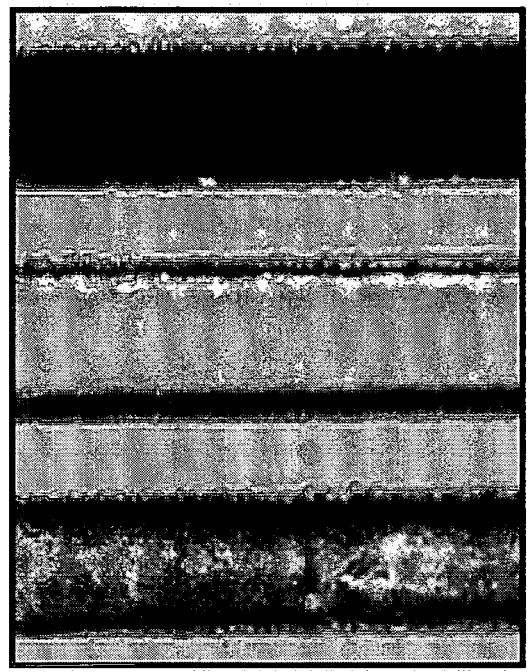

The significant signal enhancement due to this flow-based method is illustrated in the SPR microscope images in FIG. 3. The left image (FIG. 3A) consists of three microchannels filled with PBS (identified as the "dark" regions). The "bright" regions separating the three channels represent the adhesive and Mylar™ layers comprising the microchannel walls. As described above, all channels were exposed to anti-cortisol antibodies followed by a BSA blocking layer. From top to bottom, c-HRP solutions of the following concentrations were incubated within the microchannels: 0 µg/ml (top channel in FIGS. 3A and B), 0.5 µg/ml (middle channel in FIGS. 3A and B), and 0.07 µg/ml (bottom channel in FIGS. 3A and B). Thus, the SPR sensor surface in each channel was effectively functionalized with varying amounts of enzyme. The top channel served as a control channel, where the c-HRP incubation step was replaced by a BSA incubation step. The right image (FIG. 3B) depicts the same microchannels after introduction of TMB and the subsequent rinse with PBS, as described in the experimental method above (see Example 1).

As is obvious from the images in FIGS. 3A and 3B, the top control channel that contained only substrate showed little change in SPR signal after exposure to TMB. In contrast, the bottom two channels that contained both enzyme and substrate showed appreciable changes in signal. Furthermore, the change in percent reflectivity (% R) due to precipitate formation was significantly greater in the middle channel, which was exposed to a higher concentration of c-HRP than the bottom channel. Visual inspection of the microchannels showed that the presence of blue precipitate within the channels correlated with the reflectivity signal in the SPR images.

Figure 4:
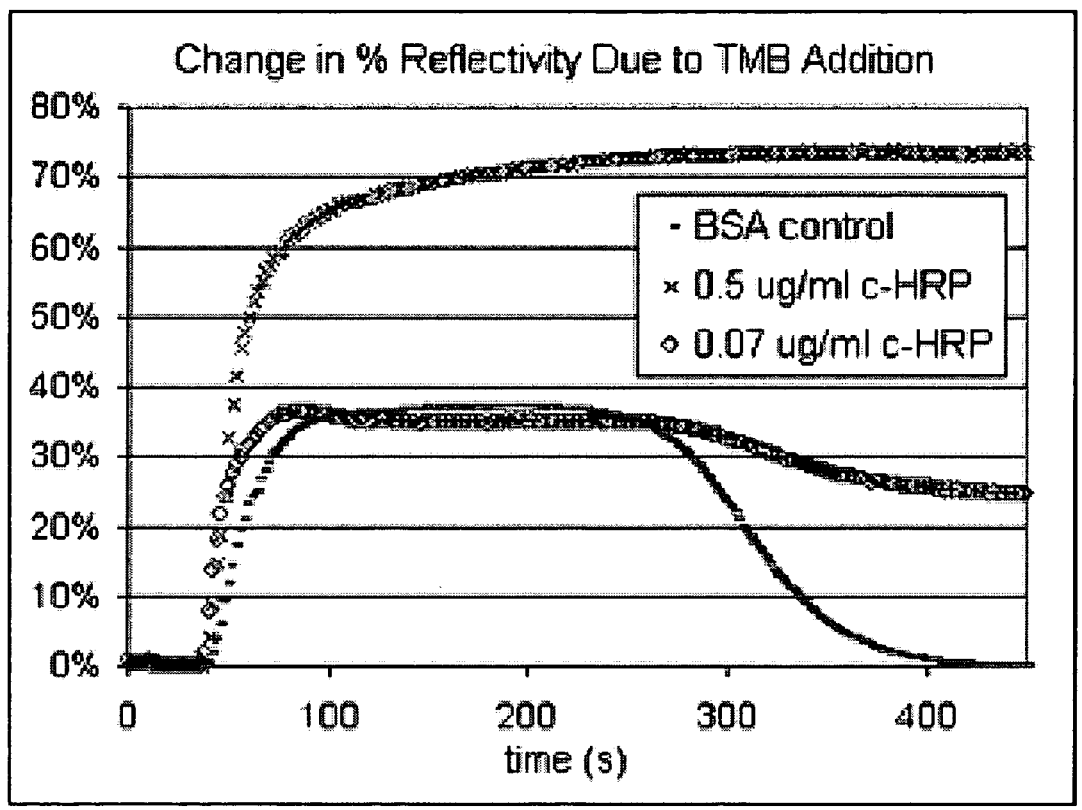
FIG. 4 illustrates SPR imaging results showing a change in percent reflectivity over the course of substrate addition and PBS rinse stages for regions in each of the three microchannels. Each of the three microchannels was exposed to various concentrations of enzyme labeled reagent prior to substrate addition.

The change in percent reflectivity over the course of the TMB addition and PBS rinse stages for representative regions in each of the three microchannels above is presented in FIG. 4. As discussed above, a significant increase in SPR signal intensity was observed in the enzyme-containing channels following the addition of TMB. For the higher enzyme concentration (0.5 µg/ml), this corresponded to an increase in percent reflectivity of over 70% (see upper line in FIG. 4). As a comparison, a monolayer of antibody non-specifically adsorbed directly onto the metal sensing surface produced a change in percent reflectivity of approximately 35% (data not shown). It is noted that the response of the instrument is linear below a change in reflectivity of 25%. The 0.07 µg/ml enzyme concentration results are seen as the middle line in FIG. 4. It also noted that the BSA control channel also underwent an increase in % R during the TMB introduction (see lower line in FIG. 4). This is expected and explained by the fact that the TMB solution itself has a much higher refractive index than PBS, thereby producing a change in the effective refractive index sensed by SPR detection. In contrast to the enzyme-containing channels where the insoluble blue precipitate was formed, the SPR signal in the BSA control channel returned to baseline after rinsing with PBS. Furthermore, as indicated in FIG. 4, the precipitated product was significantly resistant to extensive rinsing at the flow rate explored. The SPR signal amplification process was also very rapid.

As illustrated in Example 1, these results demonstrate that the precipitate formed by the enzymatic reaction adsorbs to the SPR sensor surface and significantly amplifies the detection signal. A microfluidic laminar flow system involving this method has great utility in a number of SPR biosensor assays, including sandwich and competition immunoassays for a range of antigens. Quantification may be possible either through assessment of the end-point measurements before or after rinsing with buffer, or through an evaluation of the rate of precipitate formation and accumulation near the SPR sensor surface.

The extension of this SPR signal amplification method to flow has a number of advantages over previous static utilizations. For example, systems requiring continuous flow may now also realize improved detection sensitivity through the implementation of this biocatalyzed precipitation method. Furthermore, under flow conditions, a higher rate of precipitate formation may be achieved in cases where the substrate or other reagent necessary for the precipitation reaction has a large diffusion coefficient, or in cases where the substrate concentration (but not volume) is limited. A microfluidic laminar flow system may also be used to generate a concentration gradient useful for rapidly evaluating the effect of a range of substrate concentrations on the extent of precipitation. For example, the diffusion of molecules between two parallel fluid streams, each containing an essential reagent for the precipitation process (i.e. hydrogen peroxide and TMB), will create a predictable and known concentration gradient along the width of the microchannel (dimension across the two streams), causing spatial variations in the extent of the precipitation reaction.

While the above is a description of certain embodiments of the invention, various alternatives, modifications, and equivalents can be used. Therefore, the above description should not be taken as limiting the scope of the invention which is defined by the appended claims. All publications, patents, patent applications and other references cited herein are also incorporated by reference herein in their entirety.

What is claimed is:

1. A method for conducting an assay for an analyte in a test solution that may contain the analyte comprising:
    i) providing a microfluidic channel comprising a surface plasmon resonance (SPR) active surface;
    ii) immobilizing an analyte capture agent on the surface;
    iii) contacting the analyte capture agent with the test solution and an enzyme labeled reagent under conditions for the analyte capture agent to form a complex with an analyte or the enzyme labeled reagent, wherein the enzyme is capable of forming a precipitate when reacted with a precipitatable substrate;
    iv) flowing solution containing the precipitatable substrate of the enzyme through the microfluidic channel so as to contact the complex with the solution comprising the precipitatable substrate of the enzyme under conditions conducive to the formation of the precipitate product for a time period sufficient for forming the precipitate; and
    v) detecting a change in refractive index near the surface as a function of spatial position on the surface due to precipitate formation using a SPR signal, wherein the change in the refractive index at a selected location is indicative of amount of the analyte on the surface at the selected location.

2. The method of claim 1, wherein the surface plasmon resonance surface is a thin metal film.

3. The method of claim 2, wherein the thin metal film is gold, silver, aluminum or copper.

4. The method of claim 2, wherein the thin metal film is coated on a glass surface.

5. The method of claim 1, wherein the enzyme labeled reagent is the analyte of interest or an analyte binding agent.

6. The method of claim 5, wherein the analyte binding agent is an antibody, a lectin, a carbohydrate, a polynucleotide sequence, or a receptor protein.

7. The method of claim 6, wherein the antibody is a polyclonal antibody, a monoclonal antibody, an antibody antigen-binding fragment, or a recombinant antibody.

8. The method of claim 7, wherein the antibody antigen binding fragment is a Fab, $F(ab')_2$, a Fab', or a Fv fragment.

9. The method of claim 5, wherein the enzyme is a peroxidase or a phosphatase.

10. The method of claim 9, wherein the enzyme is horseradish peroxidase or alkaline phosphatase.

11. The method of claim 10, wherein the substrate is tetramethyl-benzidine or 5-bromo-4 chloro-3-indolylphosphate with nitroblue tetrazolium.

12. The method of claim 5, wherein the analyte capture agent and the enzyme labeled analyte binding agent are specific for the analyte of interest.

13. The method of claim 12, wherein the analyte capture agent and the enzyme labeled analyte binding agent are monoclonal antibodies.

14. The method of claim 1, wherein the analyte capture agent is an antibody, a lectin, a carbohydrate, a polynucleotide sequence, or a receptor protein.

15. The method of claim 14, wherein the antibody is a polyclonal antibody, a monoclonal antibody, an antibody antigen binding fragment, or a recombinant antibody.

16. The method of claim 15, wherein the antibody antigen binding fragment is a Fab, F(ab')$_2$, a Fab', or a Fv fragment.

17. The method of claim 14, wherein the analyte capture agent is a monoclonal antibody and the enzyme labeled reagent is the analyte of interest.

18. The method of claim 17, wherein the enzyme labeled analyte is added prior to the test solution for a time period sufficient for complex formation; and wherein contact with analyte in the test solution competes with the enzyme labeled analyte for binding to the antigen capture agent.

19. The method of claim 14, wherein the analyte capture agent is a polynucleotide sequence and the enzyme labeled reagent is a nucleic acid probe.

20. The method of claim 1, wherein the assay is a high throughput assay.

21. A method for conducting an assay for a plurality of analytes comprising:
   i) providing a microfluidic channel comprising a surface plasmon resonance active surface;
   ii) immobilizing a plurality of analyte capture agents on the surface in discrete regions to form an array;
   iii) contacting the analyte capture agents with a test solution and a plurality of enzyme labeled reagents specific for the analytes of interest, under conditions for analyte capture agents to form specific complexes with the analytes and the enzyme labeled reagents, wherein the plurality of enzyme labeled reagents are capable of forming a precipitate when reacted with a precipitatable substrate;
   iv) flowing solution having precipitatable substrate of the enzymes through the microfluidic channel so as to contact the complexes with the precipitatable substrate under conditions conducive to formation of the precipitate product for a time period sufficient for precipitate formation; and
   v) detecting a change in refractive index near the surface as a function of spatial position on the surface due to precipitate formation, at each discrete region using a SPR signal, wherein the change in the refractive index at a selected location is indicative of amount of the analyte of interest on the surface at the selected location.

22. The method of claim 21, wherein the surface plasmon resonance surface is a thin metal film.

23. The method of claim 22, wherein the thin metal film is gold, silver, aluminum or copper.

24. The method of claim 23, wherein the thin metal film is coated on a glass surface.

25. The method of claim 21, wherein the enzyme labeled reagents are an analyte of interest or an analyte binding agent.

26. The method of claim 25, wherein the analyte binding agents are antibodies, lectins, carbohydrates, polynucleotide sequences, or receptor proteins.

27. The method of claim 26, wherein the antibodies are polyclonal antibodies, monoclonal antibodies, antibody antigen-binding fragments, or recombinant antibodies.

28. The method of claim 27, wherein the antibody antigen-binding fragments are Fab, F(ab')$_2$, Fab' or Fv fragments.

29. The method of claim 25, wherein the enzyme is a peroxidase or a phosphatase.

30. The method of claim 25, wherein the enzyme is horseradish peroxidase or alkaline phosphatase.

31. The method of claim 30, wherein the substrate is tetramethyl-benzidine or 5-bromo-4 chloro-3-indolylphosphate with nitroblue tetrazolium.

32. The method of claim 26, wherein the analyte capture agents are monoclonal antibodies and the enzyme labeled reagents are the analytes of interest.

33. The method of claim 32, wherein the enzyme labeled analyte is added prior to the test solution for a time period sufficient for complex formation; and wherein contact with analyte in the test solution competes with the enzyme labeled analyte for binding to the antigen capture agent.

34. The method of claim 21, wherein the analyte capture agent is an antibody, a lectin, a carbohydrate, a polynucleotide sequence, or a receptor protein.

35. The method of claim 34, wherein the antibody is a polyclonal antibody, a monoclonal antibody, an antibody antigen-binding fragment, a recombinant antibody.

36. The method of claim 35, wherein the antibody antigen-binding fragment is a Fab, F(ab')$_2$, a Fab', or a Fv fragment.

37. The method of claim 21, wherein the analyte capture agent and the enzyme labeled analyte binding agent are specific for the analyte of interest.

38. The method of claim 37, wherein the analyte capture agent and the enzyme labeled analyte binding agent are monoclonal antibodies.

39. The method of claim 21, wherein the analyte capture agent is a polynucleotide sequence and the enzyme labeled reagent is a nucleic acid probe.

* * * * *

UNITED STATES PATENT AND TRADEMARK OFFICE
CERTIFICATE OF CORRECTION

PATENT NO. : 7,405,054 B1
APPLICATION NO. : 11/301720
DATED : July 29, 2008
INVENTOR(S) : Melissa Hasenbank et al.

It is certified that error appears in the above-identified patent and that said Letters Patent is hereby corrected as shown below:

Column 1, line 16, please delete,

"Aspects of the present invention were conducted with funding provided by the National Institutes of Health, National Institute of Dental and Craniofacial Research under Grant Nos. 5U01 DE0-14971-03 and DE07023-28. The Government may have certain to rights in the claimed invention."

and insert

-- This invention was made with government support under grants 5U01 DE014971-03 and DE 07023-28 awarded by the National Institutes of Health. The government has certain rights in the invention. --

Signed and Sealed this

Eleventh Day of November, 2008

JON W. DUDAS
*Director of the United States Patent and Trademark Office*